United States Patent [19]

Mikitenko et al.

[11] 4,299,999

[45] Nov. 10, 1981

[54] PROCESS FOR THE PREPARATION AND ISOLATION OF METHYL-TERT-BUTYL ETHER

[75] Inventors: Paul Mikitenko, Noisy le Roi; Lionel Asselineau, Paris, both of France

[73] Assignee: Institut Francais du petrole, Rueil-Malmaison, France

[21] Appl. No.: 148,341

[22] Filed: May 9, 1980

[30] Foreign Application Priority Data

May 9, 1979 [FR] France .............................. 79 11958

[51] Int. Cl.$^3$ ...................... C07C 41/05; C07C 41/34
[52] U.S. Cl. .................................. 568/697; 568/699; 203/42; 203/66; 203/70; 203/78
[58] Field of Search ................................ 568/697, 699

[56] References Cited

U.S. PATENT DOCUMENTS

| | | | |
|---|---|---|---|
| 2,480,940 | 9/1949 | Leun et al. | 260/692 |
| 3,912,463 | 10/1975 | Kozlowski et al. | 568/697 |
| 4,118,425 | 10/1978 | Herbstman | 568/697 |

*Primary Examiner*—Howard T. Mars
*Attorney, Agent, or Firm*—Millen & White

[57] ABSTRACT

Process for producing and isolating methyl-tert-butyl ether (MTBE) comprising etherifying isobutene, contained in a $C_4$ hydrocarbons mixture, with methanol in the presence of a recycle stream of $C_5$ and/or $C_6$ hydrocarbons, separating from the obtained reaction product, by fractionation, at least the major part of the unconverted $C_4$ hydrocarbons, and discharging them, and fractionating the remaining product in two fractions, one of which contains an azeotrope of methanol with the $C_5$ and/or $C_6$ hydrocarbons and is recycled, the other fraction containing the purified MTBE.

8 Claims, 1 Drawing Figure

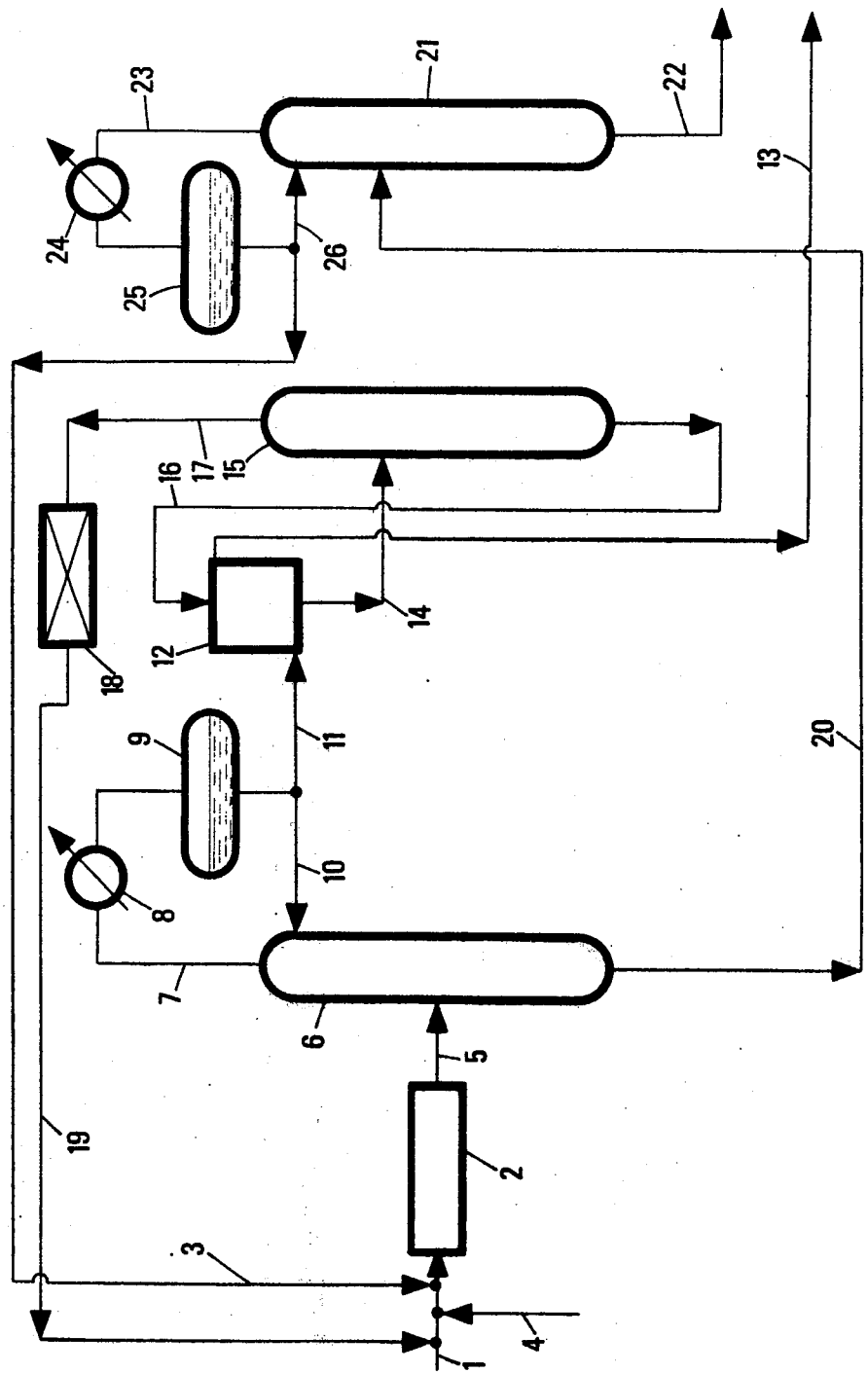

PROCESS FOR THE PREPARATION AND ISOLATION OF METHYL-TERT-BUTYL ETHER

This invention concerns the preparation and isolation of methyl-tert-butyl ether, a valuable compound which can be used particularly as a blending agent for gasolines, in view of its high octane number.

It is well known to react isobutene with methanol in the presence of acid catalysts to produce methyl-tert-butyl ether (MTBE). (See for example U.S. Pat. No. 2,480,940 and No. 3,037,052).

Isobutene is used in most cases as a $C_4$ cut containing, in addition to isobutene, other monoolefins and saturated hydrocarbons. Such a cut may be produced, for example, from a steam-cracking or a hydrocarbon dehydrogenation unit. Its isobutene content is, for example, from 10 to 60% by weight or more.

The reaction being balanced, there is normally obtained, in the reaction product, in addition to MTBE, methanol and isobutene, other hydrocarbons of the $C_4$ cut. The use of a methanol excess, in order to displace the reaction equilibrium does not change, in fact, the reaction conditions since the effluent still contains methanol, the hydrocarbons of the $C_4$ cut which were present with the isobutene, and MTBE.

The problem of fractionating this mixture is difficult in view of the formation of azetropes: methanol/MTBE azeotropes and $C_4$ hydrocarbons/methanol azeotropes.

A known process (French Pat. No. 2,356,620) consists, after having removed the unreacted $C_4$ hydrocarbons, of distilling the methanol/MTBE azeotrope under superatmospheric pressure; this azeotrope is recycled to the reactor for manufacturing MTBE and purified MTBE is recovered from the bottom. This technique has the disadvantage of recycling to the reactor a substantial amount of MTBE, which results in a change of the reaction equilibrium in the wrong direction and further reduces the conversion rate of the reactants.

Another known technique, applicable exclusively when the effluent to be distilled contains more than 15% of methanol (according to U.S. Pat. No. 3,940,450), consists of proceeding in 5 distillation steps. There is first distilled the residual isobutene, then a mixture of methanol and MTBE as an azeotrope, while recovering methanol at the bottom; the azeotrope is then distilled again under a pressure from 1 to 2.4 atmospheres abs., in the presence of n-pentane; at the top there is recovered a methanol/pentane azeotrope and, at the bottom, MTBE. This azeotrope, at the preferred pressure of 1 bar absolute, contains 9% of methanol and 91% of n-pentane, which requires the use of a large amount of n-pentane if it is desired to remove all the methanol. The azeotrope is washed with water, thereby providing two phases which are separated; the aqueous phase is fractionated by distillation to water and methanol, and the latter is recycled to the reactor for the production of MTBE; the pentane phase is also fractionated by distillation to water and pentane, and the latter is recycled to the third distillation step. This method requires an expensive apparatus and a high power consumption.

The process of the invention avoids the disadvantages of the prior technique. It comprises the following step:

(1)—An etherification zone is fed with a mixture containing (a) methanol, (b) a $C_4$ hydrocarbon mixture containing isobutene and (c) a recycle stream containing methanol and at least one $C_5$ and/or $C_6$ hydrocarbon and the reaction effluent containing unconverted $C_4$ hydrocarbons, unconverted methanol, MTBE and a $C_5$ and/or $C_6$ hydrocarbon, is discharged from the reactor.

(2)—This reaction effluent is fractionated into a first product or top product, containing at least the major part of the unconverted $C_4$ hydrocarbons and a second product or bottom product containing methanol, MTBE and the $C_5$ and/or $C_6$ hydrocarbon.

(3)—The top product from step (2) is discharged.

(4)—The bottom product from step (2) is fractionated to a top product containing a methanol/$C_5$ and $C_6$ hydrocarbon azeotrope and a bottom product containing purified MTBE.

According to an alternative embodiment of this process, the top product discharged from step (3) is washed with water and there are recovered two phases which are separated; the hydrocarbon phase is discharged and the aqueous phase, containing methanol, may be subjected to fractionation to obtain methanol at the top, which may be recycled to the reactor, optionally after drying, and water at the bottom, which may be re-used in the washing step.

Thus the process is mainly based on the known use of a $C_5$ and/or $C_6$ hydrocarbon(s) as azeotropic agent for carrying away methanol, but this use is performed under new conditions, resulting in a much more simple process. As a matter of fact, two distillation columns are sufficient for carrying out the process in its simpler embodiment. A third column may be provided, in the above alternative embodiment of the process, but the latter may be of small size. As a matter of fact, when proceeding to the distillation of $C_4$ hydrocarbons under a relatively low pressure, the stripping of methanol remains low.

The reaction of isobutene with methanol is well known and need not to be described here in detail. Reference can be made, for example, to U.S. Pat. No. 3,037,052. A preferred catalyst consists of a solid ion exchange resin in acid form, particularly a macroreticular sulfonic resin. The temperature usually ranges from 40° to 120° C., and the operating pressure is sufficient to maintain the reactants at least partly in the liquid phase. The molar ratio methanol/isobutene is preferably higher than 1, for example from 1.01 to 1.30.

The distillation of the unconverted $C_4$ hydrocarbons is performed under normal pressure or superatmospheric pressure, for example under 1–16 bars abs. The lower the pressure, the smaller the amount of methanol carried away; conversely, too low a pressure would decrease the condensation temperature of the vapors and require the use of a cooling agent at a low temperature level and associated refrigeration expenses. It is more economical to make use of water as the cooling agent with the corresponding requirement in most cases of proceeding under superatmospheric pressure. For practical reasons, pressures from 4 to 16 absolute atmospheres are preferred.

The distillation temperature depends on the selected pressure; provided this condition is fulfilled, it is preferred to make use of top of the column temperatures from 40° to 120° C., corresponding to bottom of the column temperatures from about 100° to 175° C.

The efficiency of the distillation is improved by allowing a portion of the hydrocarbon condensate to reflux in the column, the reflux rate (ratio of the refluxed liquid hydrocarbons volume to the volume of the distillate) being, for example, from 0.1 to 5.

The distillation of the methanol/$C_5$ and/or $C_6$ hydrocarbon azeotrope is performed under any pressure, for example from 1 to 20 bars abs., preferably 2.5 to 16 bars abs. The other conditions being unchanged, the pressure may be lower with a $C_6$ hydrocarbon than with a $C_5$ hydrocarbon, lower with a straight-chain hydrocarbon than with a branched hydrocarbon.

The use of a pressure higher than 2.5 bars is particularly advantageous in view of an increased proportion of methanol in the azeotrope, which may reach or even exceed 25% by weight.

In this case also, the distillation temperature depends on the selected pressure. By way of illustration, the top temperatures in most cases range from 100° to 140° C and the bottom temperatures from 125° to 175° C.

A portion of the top condensate is advantageously allowed to reflux into the column, the reflux rate being for example from 0.1 to 5.

When proceeding to a water-wash of the distilled residual $C_4$ cut, this wash may be preformed by any known technique, for example by admixture in line, by counter-current contact in a column etc. . . . ; the two resultant phases are separated by any known means, for example by mere decantation. The aqueous wash phase is distilled and the methanol recovered at the top may be dried by any known means, before being fed back to the reactor. As a drying agent, there can be used, for example, silica gel or molecular sieves.

The $C_5$ and/or $C_6$ hydrocarbon may be a pure individual hydrocarbon, for example n-pentane, isopentane, n-hexane or isohexane, or a mixture of several $C_5$ and/or $C_6$ hydrocarbons. However, the saturated hydrocarbons are preferred in order to avoid side reactions and more particularly the $C_5$ hydrocarbons are preferred, in view of the more favorable boiling point of the resultant azeotrope.

The invention is illustrated by the FIGURE of the accompanying drawing, given by way of non-limitative example.

The fresh charge of $C_4$ fraction and methanol is fed through line 1 to reactor 2. The methanol/$C_5$ and/or $C_6$ hydrocarbon azeotrope is also fed to this reactor through line 3. A further amount of $C_5$ and/or $C_6$ hydrocarbon may be supplied, if necessary, through line 4. The effluent (line 5) is fed to the distillation column 6; at the top thereof, unconverted $C_4$ hydrocarbons are separated and discharged through line 7; they pass through the condenser 8 and the reflux drum 9. A portion thereof is then fed to the column, as reflux, through line 10; the remaining portion (line 11) may be discharged or washed with water in contactor 12. The washed hydrocarbons are discharged through line 13. The wash water is fed through line 14 to the distillation column 15; water is recycled to the wash step through line 16 and the top effluent, of high methanol content, is discharged through line 17 and passes through the dryer 18 and may be recycled to reactor 2 through line 19.

The bottom product of column 6 is fed through line 20 to the distillation column 21 and MTBE is recovered from the bottom through line 22. The top effluent (line 23) is condensed in the condenser 24 and is fed to the reflux drum 25. A part of the azeotrope is recycled therefrom to the reactor through line 3, whereas the other portion is fed back to column 21 as reflux (line 26).

The following non-limitative examples illustrate the invention.

EXAMPLE 1

A MTBE synthesis reactor is fed with a butadiene-free steamcracking $C_4$ cut, with methanol and with pentane of technical grade, initially added to the system but produced under stabilized operating conditions as a distillate recycled from the distillation column (21) to which a small further amount is added to compensate for losses. The effluent from said reactor, having the following composition by weight:

| | |
|---|---|
| $C_4$ hydrocarbons | 30.6 |
| Pentane | 19.3 |
| MTBE | 43.5 |
| Methanol | 6.1 |
| Miscellaneous | 0.5 | is fed, at a rate of 5000 g/h, to a distillation column of a 110 mm diameter, comprising 50 plates with 2 bubble caps, operating under a pressure of 6 atm. The operation of the column is so regulated as to obtain, at the top, nearly all the hydrocarbons with 4 carbon atoms, while leaving at the bottom pentane and MTBE. Under these conditions, there is established in the column a temperature distribution whose limit values are 54° C. at the top and 110° C. at the bottom. The condensed top vapors provide a MTBE-free distillate (<50 ppm by weight of MTBE) but containing a small amount of methanol which, if necessary, may be removed by water washing.

The residue, whose composition is given in Table I, second column, and which constitutes the charge of column (21) is fed, at a rate of 3440 g/h to the distillation column (21) having 70 plates with bubble caps, operated under a pressure of 16 atmospheres. Under these conditions, a temperature distribution prevails within the column, ranging from 136° C. (top) to 175° C. (bottom); the compositions of the effluents are given in Table II (3rd and 4th columns).

TABLE I

| | CHARGE | TOP | BOTTOM |
|---|---|---|---|
| $C_4$ Hydrocarbons | 1.1 | 2.8 | — |
| Pentane | 28.1 | 75 | 0.5 |
| MTBE | 63.1 | 3.5 | 98.2 |
| Methanol | 7 | 18.7 | 0.2 |
| Miscellaneous | 0.7 | — | 1.1 |

The top effluent from the column is recycled to the reactor for the MTBE synthesis while the bottom fraction is discharged from the unit as purified MTBE product.

EXAMPLE II

The operation described in example 1 is reproduced except that the agent for carrying away methanol is no longer pentane but a mixture of isohexanes.

The first distillation wherein the $C_4$ hydrocarbons which have not reacted with methanol can be separated at the top of the column, is achieved under the same conditions as those precedingly described (50 plates, 6 atm).

The second distillation is performed under a pressure of 10 atmospheres and so regulated as to separate, at the top of the column, practically all isohexanes and methanol and, at the bottom, the MTBE. Under these conditions, the top and bottom temperatures are respectively 118° and 150° C. The compositions of the charge and of the effluents are given in the following Table:

TABLE II

|  | CHARGE | TOP | BOTTOM |
|---|---|---|---|
| $C_4$ Hydrocarbons | 1.2 | 4.1 | — |
| Isohexanes | 18.6 | 61.8 | 0.7 |
| MTBE | 71.5 | 7.3 | 98 |
| Methanol | 7.9 | 26.8 | 0.2 |
| Miscellaneous | 0.8 | — | 1.1 |

The top effluent from the column is recycled to the reactor for the MTBE synthesis while the bottom fraction is discharged from the unit as purified MTBE product.

What is claimed is:

1. A process for producing and isolating methyl-tert-butyl ether (MTBE) comprising the following steps of:
   (1)—feeding an etherification zone with a mixture containing (a) methanol, (b) a mixture of $C_4$ hydrocarbons containing isobutene and (c) a recycle stream containing methanol and at least one $C_5$ and/or $C_6$ saturated hydrocarbon and discharging from the reactor a reaction effluent containing the unconverted $C_4$ hydrocarbons, unconverted methanol, MTBE and the $C_5$ and/or $C_6$ hydrocarbon;
   (2)—fractionating said reaction effluent into a first product or top product containing at least the major part of the unconverted $C_4$ hydrocarbons and a second product or botom product containing methanol, MTBE and the $C_5$ and/or $C_6$ hydrocarbon;
   (3)—discharging the top product from step (2); and
   (4)—fractionating the bottom product from step (2) into a top product containing a methanol/$C_5$ and/or $C_6$ hydrocarbon azeotrope and a bottom product containing the purified MTBE.

2. A process according to claim 1, wherein the top product discharged from step (2) is washed with water and two phases are recovered and separated, which consist of a hydrocarbon phase essentially formed of unconverted $C_4$ hydrocarbons, which is discharged, and an aqueous phase, containing methanol, which is fractionated to recovered methanol and water, the recovered methanol being fed back to step (1) and the water fed back for washing the top product discharged from step (2).

3. A process according to claim 1, wherein the fractionation of step (2) is conducted by distillation under a pressure from 4 to 16 bars abs.

4. A process according to claim 3, wherein the operation is conducted at a reflux rate from 0.1 to 5.

5. A process according to claim 1, wherein the fractionation of step (4) is performed under a pressure from 2.5 to 16 bars abs., at a reflux rate from 0.1 to 5.

6. A process according to claim 2, wherein the recovered methanol is subjected to drying before being fed back to step (1).

7. A process according to claim 1, wherein a cut of $C_5$ saturated hydrocarbons is used in step (1).

8. A process according to claim 1, wherein an isohexane cut is used in step (1).

* * * * *